United States Patent
Ronholdt et al.

(10) Patent No.: US 8,303,898 B2
(45) Date of Patent: *Nov. 6, 2012

(54) APPARATUS AND METHODS FOR TREATING ALLOGRAFT PRODUCTS

(75) Inventors: Chad J. Ronholdt, Aurora, CO (US); Simon Bogdansky, Littleton, CO (US); Alan Hooks, Commerce City, CO (US)

(73) Assignee: Allosource, Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/880,955

(22) Filed: Sep. 13, 2010

(65) Prior Publication Data

US 2011/0086383 A1    Apr. 14, 2011

Related U.S. Application Data

(60) Continuation of application No. 12/034,150, filed on Feb. 20, 2008, now Pat. No. 7,794,653, which is a division of application No. 11/557,393, filed on Nov. 7, 2006, now Pat. No. 7,658,888.

(60) Provisional application No. 60/757,914, filed on Jan. 10, 2006.

(51) Int. Cl.
*A61L 2/00* (2006.01)
*B06B 1/00* (2006.01)
*B08B 3/00* (2006.01)

(52) U.S. Cl. ............... 422/128; 422/1; 422/20; 422/28; 422/127; 134/184; 134/200

(58) Field of Classification Search ............... 422/1, 28, 422/20, 127–128, 292, 301; 134/184, 200
See application file for complete search history.

(56) References Cited

U.S. PATENT DOCUMENTS

| | | | |
|---|---|---|---|
| 2,194,375 A | | 3/1940 | Zimarik |
| 3,135,275 A | | 6/1964 | Baldwin et al. |
| 3,638,666 A | | 2/1972 | Fishman |
| 4,920,055 A | | 4/1990 | Dasgupta |
| 5,447,171 A | | 9/1995 | Shibano |
| 6,272,770 B1 | * | 8/2001 | Slutsky et al. ............ 34/596 |
| 6,691,536 B2 | | 2/2004 | Severns et al. |
| 7,658,888 B2 | | 2/2010 | Ronholdt et al. |
| 7,776,291 B2 | | 8/2010 | Klein |
| 7,794,653 B2 | * | 9/2010 | Ronholdt et al. ........... 422/20 |
| 2002/0043893 A1 | | 4/2002 | Puskas |

(Continued)

FOREIGN PATENT DOCUMENTS

| | | |
|---|---|---|
| DE | 1091076 | 10/1960 |
| JP | 05137884 A | 6/1993 |

OTHER PUBLICATIONS

English Abstract for JP 05137884 A; inventor: Ohashi, et al.; published Jun. 1993.

(Continued)

*Primary Examiner* — Jill Warden
*Assistant Examiner* — Monzer Chorbaji
(74) *Attorney, Agent, or Firm* — Sheridan Law LLC

(57) ABSTRACT

Apparatus for treating allografts, having a sonication tank configured to transmit ultrasonic energy to the interior of the tank; a treatment canister rotatably positioned in said sonication tank, and configured to receive allografts therein; and a treatment fluid source in fluid communication with said treatment canister. Methods of treating allografts and methods for determining microbial contamination using the apparatus.

8 Claims, 6 Drawing Sheets

U.S. PATENT DOCUMENTS

2002/0185150 A1* 12/2002 Namerikawa et al. .......... 134/1
2003/0029474 A1   2/2003 Gibbs et al.
2004/0037735 A1*  2/2004 DePaula et al. .............. 422/20
2005/0214895 A1   9/2005 Ronholdt
2005/0252255 A1  11/2005 Gray et al.

OTHER PUBLICATIONS

Smith, Bridget, "In-Tank Rotation . . . Boosts Ultrasonic Cleaning", Automatic Machining, Jul. 1999, 2 pages.
International Search Report for PCT/US2006/060660, ISA European Patent Office, May 9, 2007.

* cited by examiner

APPARATUS AND METHODS FOR TREATING ALLOGRAFT PRODUCTS

This is a continuation of prior U.S. patent application Ser. No. 12/034,150, filed Feb. 20, 2008 by Chad J. Ronholdt, et al. for METHODS FOR TREATING ALLOGRAFT PRODUCTS, now U.S. Pat. No. 7,794,653, which in turn is a divisional of prior U.S. patent application Ser. No. 11/557,393, filed Nov. 7, 2006 by Chad J. Ronholdt, et al. for APPARATUS FOR TREATING ALLOGRAFT PRODUCTS, which is now U.S. Pat. No. 7,658,888, and claims the benefit of U.S. Provisional Patent Application No. 60/757,914, filed Jan. 10, 2006, by Chad J. Ronholdt for APPARATUS AND METHODS FOR TREATING ALLOGRAFT PRODUCTS. The above-identified patent applications are hereby incorporated herein by reference.

FIELD OF THE INVENTION

The present invention relates generally to apparatus and methods for ultrasonic treatment of allograft products.

BACKGROUND OF THE INVENTION

The use of musculoskeletal allograft tissue in reconstructive orthopedic procedures and other medical procedures has markedly increased over the last decade. Over the past decade, more than five million musculoskeletal allografts have been safely transplanted. The most common allograft is bone. However, tendons, skin, heart valves and corneas are other common types of tissue allografts.

Prior to use, the allograft tissue must be treated with various agents in order to substantially eliminate microbial contamination as well as clean the tissue of residual blood constituents, bone marrow, residual connective tissue and gross musculature. A variety of cleaning processes have been developed in order to remove contaminants from the allograft and to inactivate microbial contaminants remaining on the allografts. However, these cleaning and inactivation methods are laborious and tedious, and often do not provide a high level of assurance that the allografts have been sufficiently cleaned (e.g., low or inconsistent log reductions in microbial contamination). In particular, many existing allograft cleaning processes require considerable manipulation of the allografts between steps, thus increasing the possibility of environmental cross-contamination. Existing processes also tend to be hard to regulate and control, and their efficacy can be technician dependent. Existing processes also tend to have a shielding or layering effect that can greatly reduce ultrasonic energy penetration and thus not clean as effectively. Furthermore, the shielding effect will also impede the liberation of contaminant microorganisms off of the tissues and into solution where they are more readily eradicated.

Following treatment, allograft products must be tested for bacterial contamination prior to release of the tissue for transplantation. Existing methods of assessing microbial contamination, however, suffer from the same limitations described above (e.g. considerable manipulation between steps, possibility for environmental cross-contamination, hard to regulate and control, technician dependent, etc.).

In the past, ultrasound has been utilized to reduce and/or eliminate microbial contamination of allograft products. Ultrasound is microbiostatic to most microbes, and is used primarily to reduce microbial loads from inanimate objects with specific bactericidal activity on gram-negative bacteria.

With the increased use of allograft products, there is a need to provide improved methods and apparatus for treating allografts in order to help provide the cleanest and safest allografts as well as confirm that the allografts are free from bacterial contamination.

SUMMARY OF THE INVENTION

The present invention provides an apparatus for treating allografts, comprising a sonication tank configured to transmit ultrasonic energy to the interior of the tank, a treatment canister rotatably positioned in the sonication tank, and configured to receive allografts therein, and a treatment fluid source in fluid communication with the treatment canister. In one embodiment, the treatment canister may be foraminous such that fluid within the sonication tank will pass into the treatment canister. Alternatively, the sonication tank may contain a sonication fluid and the treatment canister is sealed with respect to the sonication tank such that the sonication fluid cannot enter the interior of the treatment canister. A plurality of treatment fluid sources may be provided in selective fluid communication with the interior of the cleaning canister, and a fluid control system adapted for exchanging treatment fluid in the treatment canister without removing the allografts from the treatment canister may also be included.

In one embodiment, the apparatus may include at least first and second treatment fluid sources, with the control system adapted for delivering the first treatment fluid to the treatment canister and for replacing the first treatment fluid in the treatment canister with the second treatment fluid. A treatment fluid outlet in fluid communication with the treatment canister may also be included, along with a filter in selective fluid communication with the treatment fluid outlet. The interior of the treatment canister may also have a non-circular cross-sectional shape in a plane orthogonal to the rotational axis.

A method of treating allografts is also provided, and includes the steps of providing an ultrasonic treatment apparatus, the treatment apparatus including a sonication tank, a treatment canister rotatably mountable in the sonication tank, and at least one ultrasonic transducer configured to transmit ultrasonic energy to the interior of the tank and the treatment canister; placing one or more allografts inside the treatment canister; and exposing the allografts to at least one treatment fluid in the treatment canister while applying ultrasonic energy to the allografts and rotating the treatment canister in the sonication tank.

In one embodiment, ultrasonic energy is applied to the allografts at a frequency between about 40 kHz and about 170 kHz with a power output of between about 100 watts/gallon and about 550 watts/gallon. In another embodiment, ultrasonic energy is applied to the allografts at a frequency between about 72 kHz and about 104 kHz with a power output of between about 100 watts/gallon and about 300 watts/gallon. In one embodiment, the allografts are sonicated at a temperature of between about 20° C. and about 50° C. (i.e., the temperature of the sonication fluid). Alternatively, the allografts are sonicated at a temperature of between about 45° C. and about 50° C.

The step of exposing the allografts to at least one treatment fluid may comprise providing a treatment fluid within the treatment canister, and further comprise the step of exchanging at least a portion of the treatment fluid in the treatment canister without removing the allografts from the treatment canister. The allografts may be exposed to first and second treatment fluids, wherein the first treatment fluid is initially provided in the treatment canister and is thereafter exchanged for the second treatment fluid in the treatment canister. In one embodiment, the first and second treatment fluids are chosen from the group consisting of: detergents, enzyme solutions, antibiotic solutions, oxidizing agents, alcohols, sterile water, and mixtures of the foregoing. The treatment method may also include the steps of: providing an extraction fluid in the treatment canister; applying ultrasonic energy to the allografts while rotating the treatment canister; and analyzing the extraction fluid for microbial contamination.

BRIEF DESCRIPTION OF THE DRAWINGS

The following detailed description will be more fully understood in view of the drawings in which.

Figure 1:
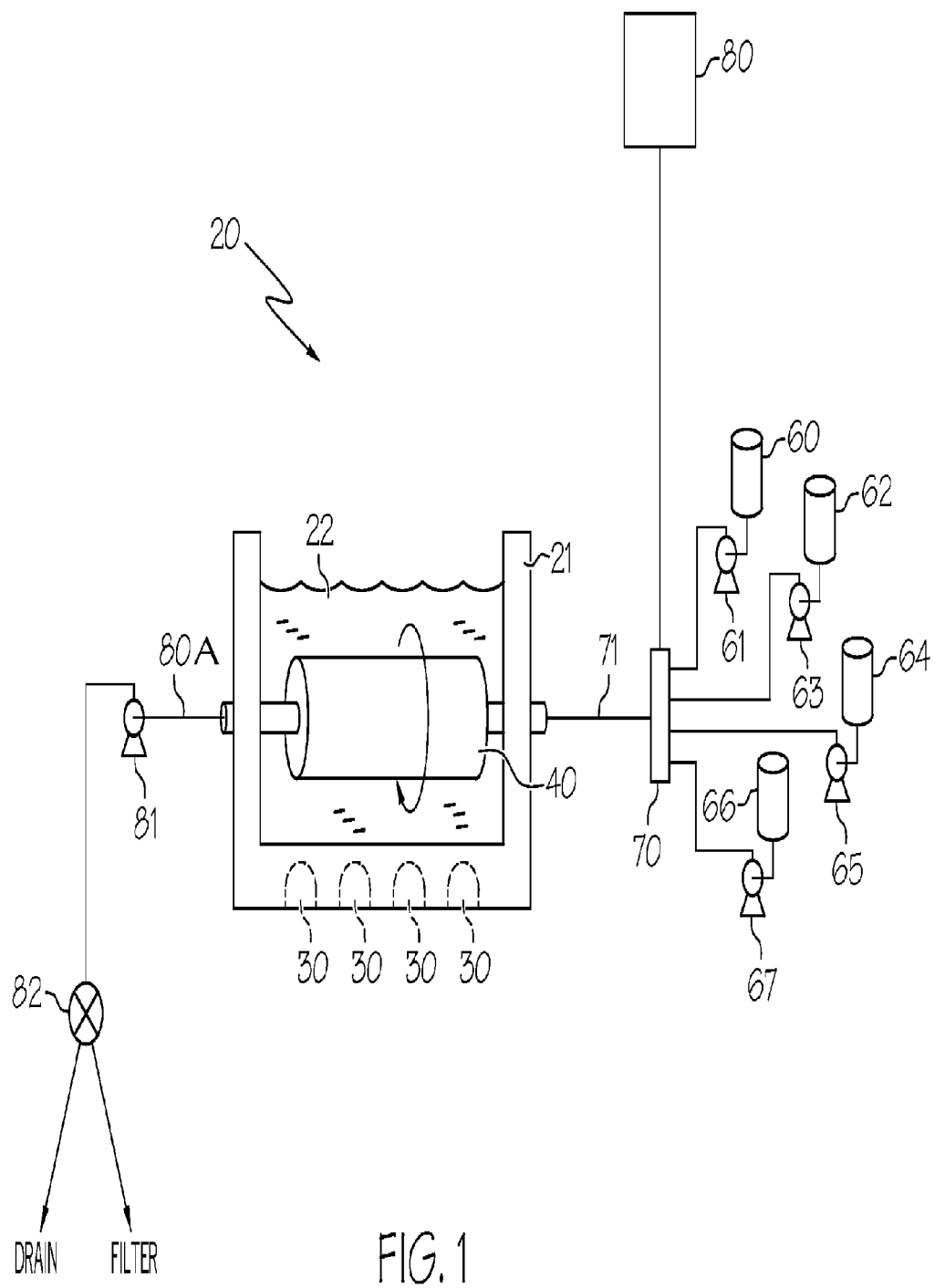
FIG. 1 is a schematic illustration of a treatment system according to one embodiment of the present invention.

The embodiments set forth in the drawing are illustrative in nature and are not intended to be limiting of the invention defined by the claims. Moreover, individual features of the drawings and the invention will be more fully apparent and understood in view of the detailed description.

DETAILED DESCRIPTION

The present invention provides apparatus and methods for treating allografts. As used herein, the terms "treating" and "treatment" are intended to encompass both the cleaning of allografts and the inactivation of microbial contaminants present on allografts (including inactivation of microbial contaminants after such contaminants have been cleaned from the allografts). The apparatus and methods of the present invention also facilitate determining microbial contamination of allograft products following treatment.

The apparatus and methods of the present invention provide treatment of allografts wherein the allografts are sonicated in a treatment canister while the allografts are rotating. Applicants have discovered that by rotating the allografts within the ultrasonic field, treatment is significantly improved. While not being limited to a theory, applicants believe that rotation prevents shielding of the ultrasonic energy since the allografts will not remain stacked on top of each other, thereby helping to ensure that all of the allografts receive maximum exposure to the ultrasonic energy and facilitates chemical reagent penetration.

During sonication and rotation, the allografts may be immersed in a variety of treatment solutions. In some embodiments, the treatment process involves sonication of the allografts in a plurality of various treatment fluids in a step-wise fashion. In addition, some embodiments of the present invention allow for various types of treatment fluids to be supplied to, and thereafter removed from, the treatment canister without opening the treatment canister. In this fashion, the allografts are not exposed to the environment or any technician manipulation during the treatment process, thereby reducing the possibility of cross-contamination. The treatment process may even be automated (or semi-automated), thereby providing greater control over the process and more consistent results which are less technician dependent.

FIG. 1 is a schematic illustration of one exemplary embodiment of a treatment apparatus according to the present invention. In particular, ultrasonic treatment apparatus 20 comprises a sonication tank 21 and a treatment canister 40 rotatably mounted in sonication tank 21. In the embodiment shown in FIG. 1, treatment canister 40 is sealed with respect to the interior of sonication tank 21 and is configured to receive one or more allografts therein. As further described herein, however, treatment canister 40 may be foraminous such that fluid within sonication tank 21 will pass into the interior of treatment canister 40.

In the embodiment of FIG. 1 wherein treatment canister 40 is sealed with respect to the interior of sonication tank 21, a sonication fluid 22 is provided within sonication tank 21. In the embodiment shown, a sufficient amount of sonication fluid 22 is provided such that treatment canister 40 is completely or at least halfway submerged. One or more ultrasonic transducers 30 are also provided, and may be located, for example, in the interior of the walls of sonication tank 21. Ultrasonic transducers 30 are configured to transmit ultrasonic energy into the interior of sonication tank 21, particularly into sonication fluid 22. Such ultrasonic energy will then be transmitted through the wall of treatment canister 40 such that allografts contained within treatment canister 40 will be subjected to the ultrasonic energy.

In one exemplary embodiment, the sonication tank configured to contain about 20 gallons of sonication fluid for the treatment of allograft tissues. In another exemplary embodiment, the sonication tank has a minimum volume of about 16 gallons and a maximum volume of about 26 gallons.

In one exemplary embodiment, the sonication tank has a height ranging from about 33 to 49 inches to the top of the tank and about 37 to 53 inches to the top of the cradle. In an alternative exemplary embodiment, the height of the sonication tank is about 33 inches to the top of the tank and about 37 inches to the top of the cradle.

In one exemplary embodiment, the rotary cleaning system can be used for the treatment on a variety of different types of products. One exemplary embodiment is the treatment of human cadaver allograft tissue.

Human cadaver allograft tissue includes, but not limited to musculoskeletal, skin, osteoarticular and/or cardiovascular tissues.

In another exemplary embodiment, the rotary cleaning system can be used to treat tissue engineered scaffolds, and polymeric or ceramic medical device implants.

Sonication fluid 22 may comprise any of a variety of compositions, such as water (an excellent medium for transmitting ultrasonic energy). Of course any of a variety of other fluids may be used, such as phosphate buffered saline or even a glycerol-based solution in order to help maintain the temperature of the sonication fluid. In addition, the sonication fluid may contain other fluids to alter the transfer of ultrasonic energy by increasing or decreasing depending on the application. The treatment canister may be made from any of a variety of materials, including metal (particularly stainless steel), glass, polymeric materials (e.g., DELRIN® acetyl resin, PTFE, etc.).

Sonication tank 21 may include one or more heaters for maintaining the temperature of sonication fluid 22. For example, the temperature of sonication fluid 22 may be maintained at a temperature of between about 20° C. and about 70° C., or between about 45° C. and about 50° C. It has been discovered that elevated temperatures facilitate the removal of protein and lipid constituents by increasing the solubility of such contaminants. Elevated temperatures also greatly improve the log reductive capabilities of oxidizing and antimicrobial agents. In one exemplary embodiment for the treatment of allograft tissues, the sonication fluid is maintained between about 45° C. to about 50° C.

Sonication tank 21, and in particular ultrasonic transducers 30, may be configured to apply constant and/or pulsed ultrasonic energy within sonication fluid 22 which in turn is transmitted into the interior of treatment canister 40. For the application of pulsed ultrasonic energy, the frequency and/or power of the ultrasonic energy may be varied during the treatment of allografts. For example, in one embodiment, sonication tank 21 is configured to apply ultrasonic energy at a frequency of between about 40 kHz and about 170 kHz. In another embodiment, the frequency of applied energy may be between about 72 and about 104 kHz, as such frequencies provide further improved cleaning of the protein and lipid constituents and liberation of viable microorganisms. In one embodiment, the power output may be between about 100 watts/gallon and about 550 watts/gallon. In another embodiment, power output is between about 100 and about 300 watts/gallon. Intensities in excess of 550 W/Gallon do provide additional microbial reductions, since such power levels result in the killing of more microbes. In one exemplary embodiment, the ultrasonic energy is supplied by 3 to 4 generators with a combined power between 2000 and 2250 W. In another exemplary embodiment for treatment of allograft products, the frequency of the applied energy is 104 kHz. As one skilled in the art will appreciate, the frequency can be modified corresponding to the treatment of other more sensitive or robust products. In one exemplary embodiment, the power output is delivered to allograft tissues at about 100 Watts/gallon. In another exemplary embodiment, the generators are located (e.g. under the sonication tank) such as to minimize exposure to any fluid leaks. Another embodiment could be that all electrical and power components may be located adjacent to or in another area to further reduce the footprint of the system facilitate servicing and maintenance procedures and to minimize any electrical hazards.

Sonication tank 21, in particular ultrasonic transducers 30 and any heater(s) associated with the tank, may also be in electrical communication with a control system for the ultrasonic treatment apparatus (e.g., controller 80) in order to control the application of ultrasonic energy and the temperature of the sonication fluid during the treatment process. In one exemplary embodiment, an intensity measuring device is wired externally or internally to the sonication tank.

A treatment fluid is also provided in the interior of treatment canister 40 in order to facilitate the application of ultrasonic energy to the allografts and optionally to perform other functions such as microbial reduction and cleaning (e.g., by killing or inactivating microbes). Ultrasonic energy from transducers 30 is transmitted through sonication fluid 22, through the wall of treatment canister 40, and thereafter through the treatment fluid contained within treatment canister 40. In this manner, the ultrasonic energy is applied to the allografts so as to liberate microorganisms as well as residual proteins, lipids and tissue particles from the allografts. Once the microorganisms are liberated from their protective areas in the allografts the chemical agents in the treatment fluid can more readily kill or inactivate the microbes out in the open. The application of ultrasonic energy with rotation facilitates the liberation of microbes from the crevices of the tissue, and thereafter the liberated microbes are exposed to the treatment fluids and higher temperatures so as to provide increased inactivation of the microbes. Depending on frequency and power output, the ultrasonic energy may also inactivate microorganisms liberated from, or remaining present on the allografts.

While the treatment fluid may comprise sterile water, applicants have also discovered that the use of various other treatment fluids will facilitate allograft cleaning and/or inactivation of microbial contaminants, as further described herein. Applicants have also discovered that the use of two or more different treatment fluids, particularly in a step-wise fashion, will further facilitate allograft treatment.

Any of a variety of treatment solutions may be used in the apparatus and methods of the present invention, including sterile water. Other suitable treatment solutions include detergent solutions, antimicrobial solutions, strong bases, oxidizing agents, alcohols, and mixtures of the foregoing, including mixtures of one or more of the foregoing with sterile water. The order of treatment solutions may effect the cleaning and microbial inactivation. Detergent, enzymatic agents and antimicrobial detergents etc. may be used first to eliminate blood, bone marrow and other organic matter. This eliminates strong reactions with oxidizing agents (e.g. hydrogen peroxide) that can create pressure within the sealed canisters and a potential hazard to the technicians. Typically, alcohol is used in the final step as a final microbial inactivation and drying agent. Sterile water can be used in between steps to further facilitate the removal of waste products and rinse the tissues of any residual chemical reagents that may impede final microbial testing.

Suitable detergent solutions include lipases, proteolytic enzymes, lysozymes, and xyloansases. Antimicrobial detergents such as one or more polymyxins (e.g., Polymyxin B may also be used). Detergents will liberate blood, bone marrow, microbes and other contaminants from the allografts. Some detergents, particularly antimicrobial detergents, also provide antimicrobial properties (i.e., kill or inactivate microbes).

Suitable antimicrobial agents include sulfonamides, fluoroquinolones (e.g. Ciprofloxacin, Norfloxacin), penicillins, cephalosporins (e.g. Cefoxitin), tetracyclines (e.g. oxytetracyclines), aminoglycosides (e.g. streptomycin, gentamycin, neomycin), macrolide antibiotics (e.g. erythromycin, clindamycin), glycopeptide antibiotics (e.g. vancomycin, teicoplanin), lantibiotics (e.g. nisin), Bacitracin and Polymyxin. Such microbial solutions may be used to kill or inactivate any bacteria present on the allografts or dislodged therefrom by the ultrasonic energy and/or detergents.

Suitable oxidizing agents include hydrogen peroxide, ozone, pericidic acid, TAEDs (N,N,N'N'-Tetra Acetyl Ethylene Diamine), sodium percarbonate, sodium perborate, sodium polyacrylate, chloride and chlorinated compounds (e.g., chlorine dioxide, sodium hypochlorite, calcium hypochlorite), and potassium permanganate. The oxidizing agents are very effective at killing or inactivating microbes liberated from or present on the allografts. They also play an important role in the "whitening" or bleaching of the allografts.

Alcohols used in treatment solutions may include isopropyl alcohol and ethanol alcohol. Alcohols not only act as microbial reduction agents, they may also be used as dehydrating agents to remove moisture from the allografts (reduces the probability of microbial survival on allografts during storage). Strong bases, particularly strong inorganic bases such as NaOH, may also be used for microbial destruction. Strong bases also provide anti-prion capabilities.

As further discussed herein, the treatment solutions may be supplied to treatment canister 40 in a step-wise fashion while ultrasonic energy is applied to the treatment canister. Alternately, the treatment canister may be removed from the sonication tank in order to exchange the treatment solution.

Treatment canister 40 in FIG. 1 is depicted as having a cylindrical shape. However, this shape is merely exemplary, as a variety of other shapes for treatment canister 40 may be utilized (as further discussed herein). Treatment canister 40 is also rotatably mounted within sonication tank 21, such that treatment canister 40 can be rotated while ultrasonic energy is applied to the allografts contained therein.

In one exemplary embodiment, the treatment canister comprises a canister. The canister may be fabricated out of materials commonly known to those skilled in the art. In another exemplary embodiment, the canister comprises a stainless steel construction. The stainless steel construction is beneficial for ease of sanitization and sterilization while allowing maximum ultrasonic energy transfer. As one skilled in the art will appreciate, the denser the material of construction, the more ultrasonic energy that is absorbed by the canister and not transferred to the products to be treated. Other exemplary materials of construction include polymers, glass and other metals.

In one exemplary embodiment, the canister is configured in a cylindrical shape and comprises a baffle system to ensure or maximize constant tissue tumbling action. In an alternative embodiment, the canister is configured in various polygonal shapes. It is believed that the polygonal shapes may obviate the need for an internal baffle system.

In another exemplary embodiment, the canister further comprises an internal basket. The internal basket is configured to facilitate the aseptic loading and removal of product from the canister while minimizing ultrasonic energy absorption. In one embodiment, the internal basket is configured to facilitate the ability of fluid delivery to the canister such that the basket rotates while the outer canister stays stationary and can be filled with fresh fluid while the expired fluid is exhausted. In one exemplary embodiment, the canister ranges from about 2-8 inches in diameter and from about 4-18 inches in length. In an exemplary embodiment for treating machine grafts, the canister is about 3 inches in diameter and about 4.5 inches in length. In another exemplary embodiment for treating cut tissue, the canister is about 6 inches in diameter and about 13 inches in length. In yet another exemplary embodiment for treating soft tissue, the canister is about five inches in diameter and about 6.5 inches in length.

Applicants have found that the combination of sonication with rotation of treatment canister 40 provides improved allograft cleaning and microbial inactivation. Rotation of treatment canister 40 during sonication will not only increase the movement of treatment fluid within canister 40, but will also cause rotation and tumbling of the allografts. The increased fluid movement also results in enhanced removal of contaminants from the allografts, while the tumbling of the allografts will not only cause more contaminants to be liberated from the allografts but will also expose more surface area of the allografts to the ultrasonic energy. Without rotation of the treatment canister, particularly when multiple allografts are positioned therein, Applicants believe that some of the allografts (or portions thereof) are shielded from the ultrasonic energy by other allografts. Applicants believe that rotation of treatment canister 40 significantly reduces (or eliminates) this shielding effect and ensures that the entire surface of each of the allografts is exposed to the ultrasonic energy. As further described herein, these effects may also be enhanced by causing treatment fluid to flow through or within treatment canister 40 during sonication.

By way of example, allografts to be treated are placed within treatment canister 40. Thereafter, a treatment fluid is supplied to treatment canister 40, such as by pouring a treatment fluid into treatment canister 40, and the canister is then sealed. The filled treatment canister 40 is then mounted within sonication tank 21 and ultrasonic energy applied to the interior of sonication tank 21 while treatment canister 40 is rotated. Ultrasonic energy is applied in treatment apparatus 20 for a period of time, and at frequency and power sufficient to dislodge contaminants (e.g., microorganisms, residual proteins, residual lipids, residual tissue particles, etc.) from the allograft and/or to inactivate microbial contaminants present on or liberated from the allografts.

In one exemplary embodiment, the volume of treatment fluid added to the canister is dependent upon the mass of the tissue that is being treated. In one particular exemplary embodiment, the volume of the treatment fluid is in a ratio of 1:2 of solution (ml) to tissue (g). In an alternative exemplary embodiment, the volume of the treatment fluid is in a ratio of 1:5 of solution (ml) to tissue (g). In yet another exemplary embodiment, the volume of the treatment fluid is in a ratio of 1:3 of solution (ml) to tissue (g). In one exemplary configuration, the volume of treatment fluid ranges from about 200 ml to about 3200 ml and the mass of tissue treated ranges from 400 g to about 6400 g per canister.

If a treatment protocol utilizing a plurality of different treatment fluids is to be followed, treatment canister 40 may be removed from sonication tank 21, and the first treatment fluid drained from canister 40. Thereafter, the second treatment fluid may be supplied to treatment canister 40 (e.g., by pouring the treatment fluid into the canister) and thereafter the canister is sealed and inserted back into sonication tank 21. Ultrasonic energy may thereafter be applied to treatment canister 40 in the same manner as described previously. This process may be repeated using any number and variety of treatment fluids, according to the predetermined protocol. If desired, after a treatment fluid is drained from treatment canister 40, sterile water (or other fluid) may be added to treatment canister 40 for purposed of rinsing or flushing the allografts in order to remove any additional contaminants liberated from the allografts and any remaining treatment solution. The sterile water wash may then be discarded and the next treatment solution added to treatment canister 40 and the canister then placed back into sonication tank 21.

It should also be pointed out that it may be desirable to simply replace a particular treatment fluid in canister 40 with fresh treatment fluid of the same composition. For example, some of the reagents used in the treatment fluid may lose strength or otherwise become less effective over time (e.g., hydrogen peroxide). In addition, waste products may accumulate in the treatment fluid (e.g., residual tissue particulates, blood, proteins, lipids, killed or inactivated microbes liberated from the allografts, etc.). Therefore, a particular treatment fluid may be drained from canister 40 in the manner described above and thereafter replaced with more of the same treatment fluid composition. This will not only replenish the particular treatment fluid in order to maintain the maximum reactivity between the treatment fluid reagents and the allografts, but will also move waste products (e.g., blood, bone marrow, microbes liberated from the allografts, etc.) away from the allografts. In this manner, the allografts will not remain in a weakened and/or contaminated treatment fluid.

It is also contemplated that treatment fluid within treatment canister 40 may be drained and replaced with the same or a different treatment fluid aseptically without opening the sealed treatment canister. For example, treatment canister 40 may be configured so as to include a drain or other fluid passageway which may be opened without unsealing the entire treatment canister. As further described herein in connection with FIG. 6, the treatment canister may include, for example, a spring loaded drain such that the treatment canister may be placed into receptacle and then pushed downwardly so as to open the spring-loaded drain. This will result in fluid within the treatment canister being drained along with any waste products present therein. Thereafter, fresh treatment fluid (either the same composition as or a different composition from the treatment drained from the canister) may be aseptically added to treatment canister 40 without opening the sealed canister.

Alternatively and as depicted schematically in FIG. 1, the treatment apparatus according to embodiments of the present invention may be configured to supply one or more treatment fluids to the interior of treatment canister 40 after the canister is mounted in sonication tank 21, thereby avoiding the need for a manual fluid exchange or otherwise requiring that canister 40 be removed from the sonication tank. In fact, particularly when more than one treatment fluid is used for treating allografts contained within treatment canister 40, an automated system for supplying treatment fluids to canister 40 may be provided.

In the embodiment of FIG. 1, a treatment fluid input line 71 provides fluid communication between one or more treatment fluid sources (e.g., treatment fluid reservoir 60) and the interior of treatment canister 40. Similarly, a treatment fluid outlet line 80A may be provided in order to allow treatment fluid to be expelled from the interior of treatment canister 40.

A plurality of treatment fluid sources may be provided, as shown in FIG. 1, such as treatment fluid reservoirs 60, 62, 64 and 66. These treatment fluid reservoirs may contain any of a variety of treatment fluids (as described previously) which are supplied to treatment canister 40 during allograft processing. For example, treatment fluids such as enzyme solutions, antibiotic solutions, oxidizing agents, and alcohols may be provided, along with one or more sources of water (e.g., sterile water).

As further detailed herein, some allograft treatment regiments include supplying a variety of treatment fluids to the allografts during sonication, with a sterile water flush of treatment canister 40 between treatment fluids. In such instances, a single source of sterile water (e.g., reservoir 66) may be provided, with water supplied to treatment canister 40 as needed. In such an embodiment, the sterile water reservoir may be larger than the other treatment fluid reservoirs.

In some embodiments, it may generally be desired to supply heated treatment fluid to treatment canister 40, even if sonication tank 21 is heated. For example, treatment fluid reservoir 60, 62, 64 and 66 may be heated in order to maintain the treatment fluids at the desired temperature (e.g., between about 37° C. and about 50° C., or even between about 45° C. and about 50° C.). Alternatively, or in addition thereto, one or more in-line heaters may be provided between treatment fluid reservoirs and treatment canister 40, before and/or after manifold 70, such as one or more heat exchangers.

It may also be desirable to filter sterilize one or more of the treatment fluids prior to the treatment fluid being supplied to treatment canister 40. For example, one or more in-line filters may be provided between the fluid treatment reservoirs and manifold 70, and/or one or more in-line filters between manifold 70 and treatment canister 40.

As mentioned previously, the treatment process may be automated, at least in part, such that treatment fluid is supplied to treatment canister 40 according to a predetermined schedule and/or without the need for an operator to open treatment canister 40 to exchange one treatment fluid for another. In the embodiment shown in FIG. 1, each of the treatment fluid reservoirs is in fluid communication with a manifold 70 (or similar device) which in turn is in communication with fluid inlet line 71. Manifold 70 is configured to control the flow of treatment fluid from the reservoirs (60, 62, 64 and 66) into the interior of treatment canister 40. A controller 80, such as a PLC or other processing device, can be used to control manifold 70. As also shown in FIG. 1, pumps 61, 63, 65 and 67 may be provided for reservoirs 60, 62, 64 and 66, respectively, in order to deliver treatment fluid from the reservoirs to manifold 70. Controller 80 may also be used to control these pumps in order to regulate the delivery of treatment fluid to canister 40.

As treatment fluid is delivered to treatment canister 40, any treatment fluid already within the canister will be expelled through fluid outlet line 80A. A pump 81 may be provided in order to facilitate removal of treatment fluid from canister 40, and may be controlled by controller 80. A valve 82 may also be provided on outlet line 80A in order to direct expelled treatment fluid to disposal or to a filtering device (e.g., a filter). In the latter case, the expelled treatment fluid is passed through the filter, and thereafter the filter analyzed for microbial contamination. In particular, after the final treatment step has been completed, the expelled final treatment may be analyzed for microbial contamination for contamination. In this manner, microbial contamination of the allografts may be assessed following the treatment process. This method of assessing microbial contamination may follow the methods described in U.S. patent application Ser. No. 10/976,078, filed Oct. 28, 2004, which is incorporated herein by way of reference.

Figure 2:
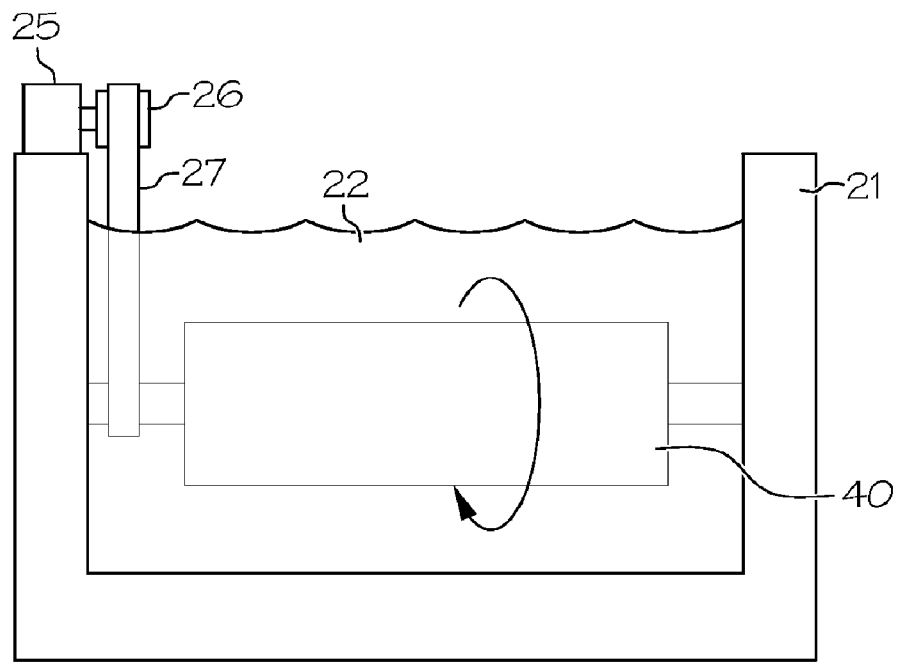
FIG. 2 is a schematic illustration of a treatment system according to another embodiment of the present invention.

Treatment canister 40 may be rotatably mounted within sonication tank 21 in a variety of manners, such as the exemplary embodiment shown in FIG. 2. In the embodiment of FIG. 2, a motor 25 and associated pulley 26 are mounted outside of tank 21, as shown. A belt 27 extends around pulley 26 and a portion of one end of the treatment canister 40. Canister 40 is rotatably mounted within tank 21 such that, as pulley 26 is rotated by motor 25, treatment canister 40 will rotate within tank 21. Of course the treatment canister may be rotated by any of a variety of mechanisms, such as direct drive, internalized gearing. In one exemplary embodiment, the canister is placed at a angle in the treatment apparatus such that the angle is configured to allow the treatment fluid to drain from the canister. This is an alternative embodiment to the utilization of pumps and/or rotation etc.

Figure 3:
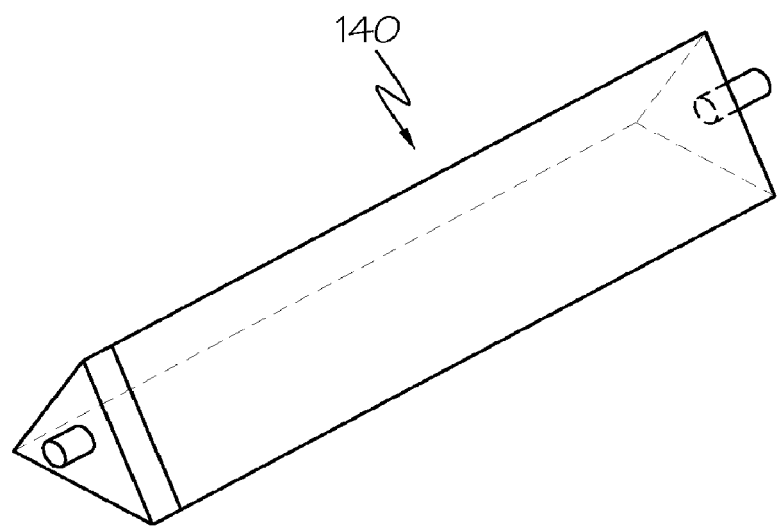
FIG. 3 is a schematic illustration of a treatment canister according to one embodiment of the present invention.

The treatment canister may have any of a variety of shapes and configurations, such as the cylindrical shape shown in FIGS. 1 and 2. Alternatively, the interior of the treatment canister may have a non-circular cross-sectional shape in a plane orthogonal to the rotational axis of the canister. For example, FIG. 3 depicts a treatment canister 140 which has a triangular cross-sectional shape. Such non-circular cross-sectional shapes for the interior of the treatment canister will not only increase turbulent fluid flow within treatment canister 140, but will also enhance the tumbling action of the allograft within the treatment canister. Both of these actions are believed to result in not only the dislodgment of additional contaminants from the allografts, but also increase the amount of surface area of the allografts exposed to the ultrasonic energy.

Figure 4:
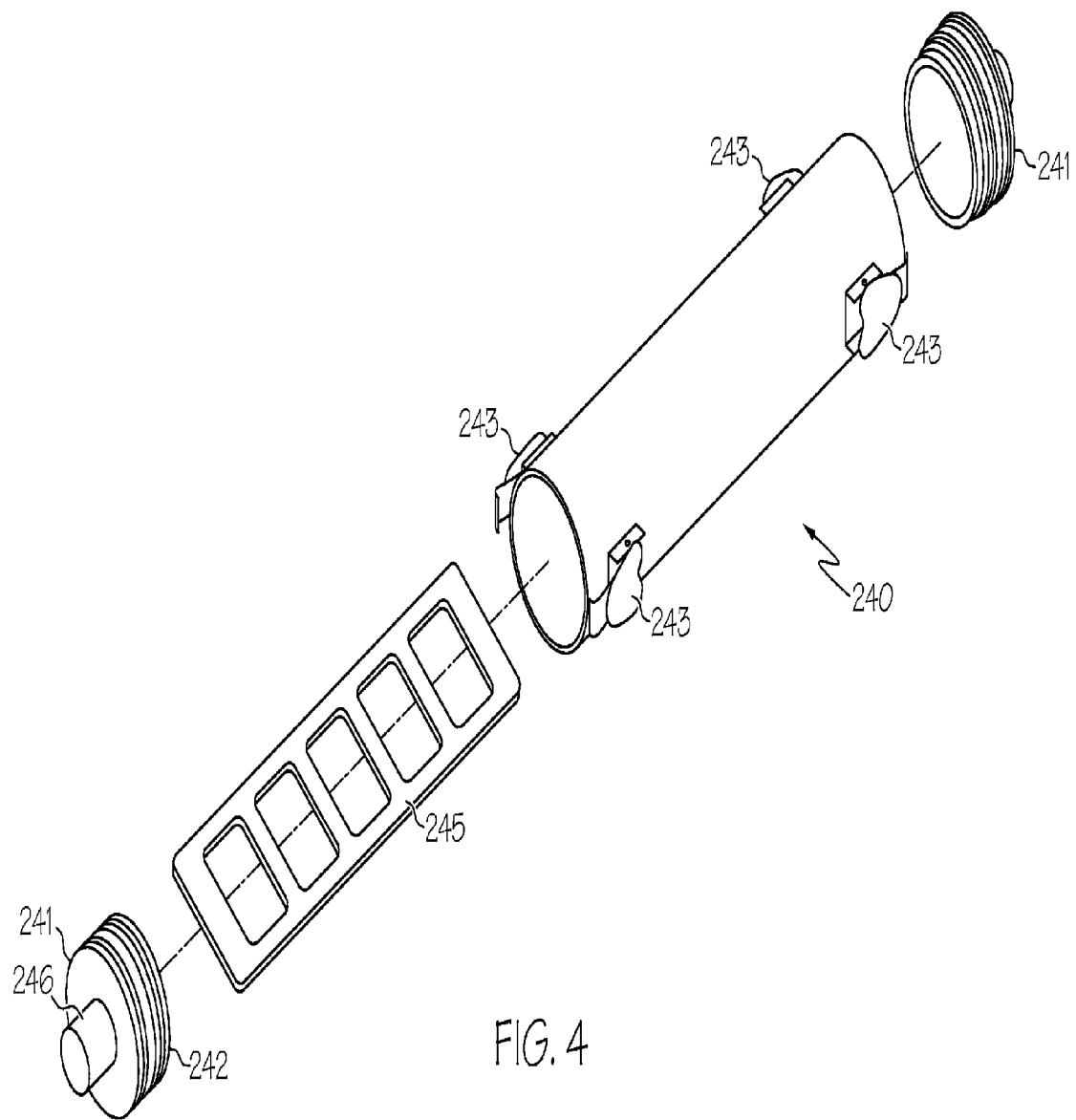
FIG. 4 is a schematic illustration of a treatment canister according to another embodiment of the present invention.

As an alternative, or in addition to a non-circular interior shape for the treatment canister, one or more baffles or other structures may be provided inside the treatment canister in order to increase the tumbling action of the allografts. For example, FIG. 4 depicts a treatment canister 240 comprising a cylindrical housing having a baffle insert 245 positioned therein. Insert 245 may have any of a variety of shapes and configurations designed to increase the tumbling of allografts within canister 240 during rotation.

Alternatively, or in addition thereto, one or more grooves or ribs may be provided on the inner surface of the treatment canister (e.g., longitudinally-extending grooves or ribs similar to the rifling of a gun barrel). Of course any of a variety of baffle structures or other features may be provided inside the treatment canister in order to increase the tumbling action of the allografts, either by physical contact with the allografts or by structures which induce turbulent treatment fluid movement within the canister. By way of further example, baffle inserts or other structures having a variety of shapes may be used, such as geometric shapes having defined edges (e.g., polygonal shapes such as octagons, pentagons, etc.). Such defined edges, whether provided on a baffle insert positioned in the treatment canister or formed in the interior surface of the treatment canister, will force the allografts to tumble as they contact the edges of the structures within the treatment canister, thus exposing additional surface area of the allografts to the ultrasonic energy.

Treatment canister 240 also includes a pair of end caps 241 which may be securely attached to opposite ends of the treatment canister after one or more allografts have been inserted into the treatment canister. One or more O-rings 242 may also be provided in order to seal the treatment canister, along with one or more latching mechanisms 243. Each end cap 241 also includes a hollow shaft 246 which extends away from the end cap and the treatment canister. Treatment fluid may be purged into or expelled from the interior of the treatment canister 240 through the hollow shafts 246.

Figure 5:
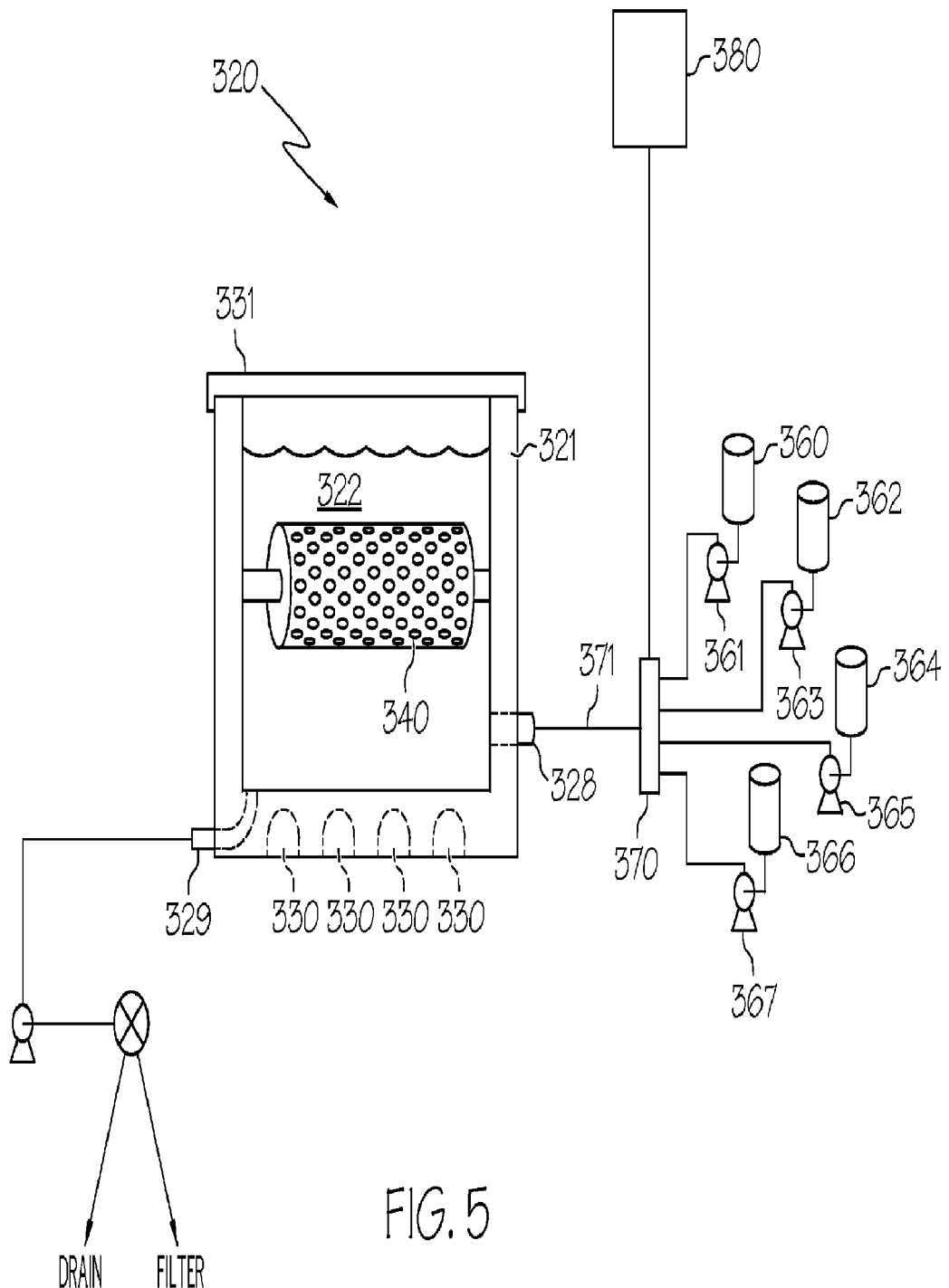
FIG. 5 is a schematic illustration of a treatment system according to another embodiment of the present invention.

FIG. 5 depicts an alternative embodiment in which treatment canister 340 is foraminous. In this embodiment, treatment fluid is supplied to sonication tank 321 and also acts as the sonication fluid during treatment. Because treatment canister 340 is foraminous, the treatment fluid will pass into the interior of treatment canister 340 and contact the allografts contained therein. Treatment canister 340 is mounted within sonication tank 321 such that it may be rotated therein during treatment, however, the mechanism for rotating canister 340 has been omitted from FIG. 5 for purposes of clarity.

Treatment fluid may be provided in sonication tank 321 manually, such as by opening lid 331 and pouring in the treatment fluid(s) according to, for example, a predetermined protocol. Alternatively, an automated treatment fluid supply system may be provided. For example, a plurality of treatment fluid reservoirs (360, 362, 364 and 366) may be provided along with corresponding pumps (361, 363, 365 and 367, respectively). A manifold 370 and controller 380 may also be provided in order to supply the proper treatment fluid to sonication tank 321 at the appropriate time according to a predetermined treatment protocol. Fluid supply line 371 is in fluid communication with a fluid inlet 328 on the sonication tank 321. Similarly, a fluid outlet 329 is provided for treatment fluid expelled from sonication tank 321. The interior of treatment canister 340 may be cylindrical, as shown. Alternatively, any of the non-circular cross-sectional shapes described previously may be used.

Figure 6:
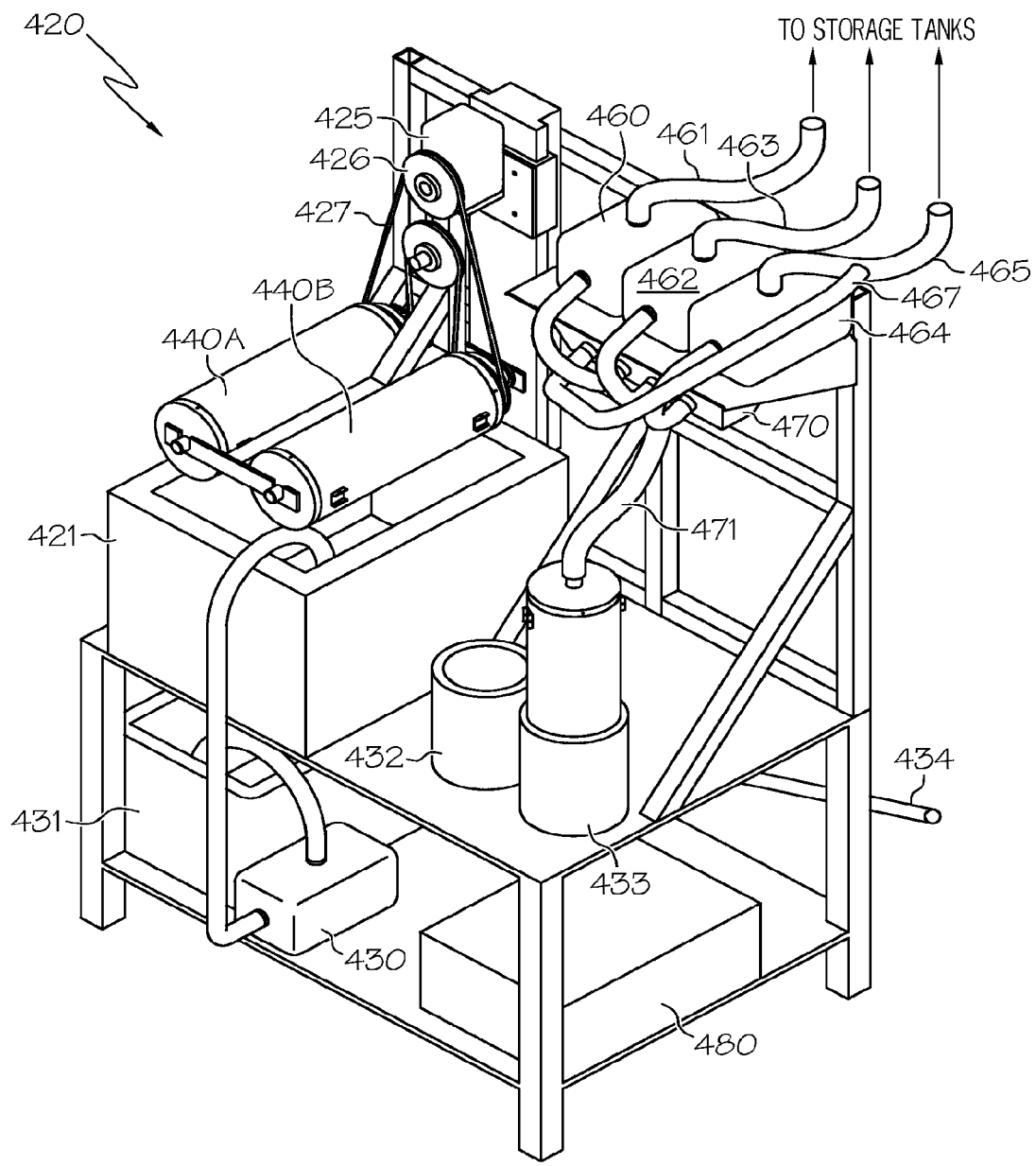
FIG. 6 is a schematic illustration of a treatment system according to yet another embodiment of the present invention.

FIG. 6 is a schematic illustration of yet another embodiment of an ultrasonic treatment apparatus 420 according to the present invention. In the embodiment of FIG. 6, system 420 is configured such that a pair of treatment canisters 440A and 440B may be simultaneously processed within sonication tank 421. In this manner allografts from two different donors may be processed simultaneously. In the embodiment of FIG. 6, the treatment canisters 440A and 440B are sealed with respect to the interior of sonication tank 421 and are configured to receive one or more allografts therein. Sonication tank 421 is configured to receive a sonication fluid, in the manner previously described. In one exemplary embodiment, the treatment apparatus comprises up to four (4) treatment canisters for simultaneous processing. As such, four (4) donor products can be treated in one processing session. In an alternative embodiment, the treatment apparatus can be configured to contain more than four treatment canisters.

Although not shown in FIG. 6, sonication tank 421 may once again include one or more heaters in order to maintain the desired temperature within sonication tank 421. The embodiment of FIG. 6 also includes a mechanism for cooling the sonication fluid in order to further maintain the desired temperature. Particularly, the system of FIG. 6 includes a cooling bath 431 located directly beneath sonication tank 421. Although not visible in FIG. 6, sonication tank 421 includes one or more drains in the bottom thereof which allows sonication fluid to flow from the bottom of tank 421 into cooling bath 431. A recirculating chiller/pump device 430 is also provided, and is in fluid communication with both cooling bath 431 and sonication tank 421, as shown. During use, sonication fluid emptying from sonication tank 421 into cooling bath 431 is chilled and returned to sonication tank 421 by recirculation chiller/pump 430. Of course, a suitable control system may be provided in order to regulate the operation of recirculating chiller/pump 430 in order to maintain the desired temperature within sonication tank 421. Since the ultrasonic transducers within or associated with sonication tank 421 will cause the temperature of the sonication fluid to rise, the use of recirculating chiller/pump 430 will further facilitate the control of the temperature of the sonication fluid during treatment. The system shown in FIG. 6 also includes a power supply 480 which will provide the necessary power for the various components of treatment system 420.

As also shown in FIG. 6, treatment canisters 440A and 440B are rotatably mounted to a carriage which may be lowered into sonication tank 421. In particular, the carriage includes a motor 425 which may be configured to not only cause the desired rotation of the treatment canisters 440A and 440B, but also to lower and raise the treatment canisters into sonication tank 421. Alternatively, raising and lowering of the treatment canisters may be done manually, or even under the automatic control of a suitable control system. Pulleys 426 and belt 427 may be used to translate rotation of the motor shaft to the treatment canisters in order to effect rotation of treatment canisters 440A and 440B in sonication tank 421. Of course FIG. 6 merely depicts one possible manner in which the treatment canisters may be rotated within sonication tank 421 during the treatment process.

In one exemplary embodiment, the rotation of the treatment canisters comprises an indirect belt drive system with a rotation speed of about 10 revolutions per minute. As one skilled in the art will appreciate, various rotation drive systems may be utilized in the present invention. Alternative rotation drive systems include, but are not limited to direct drive systems (i.e., with gears or solid drive systems) having a variable system with rotation speeds of between 0.1 and 60 revolutions per minute. In one exemplary embodiment for treatment of allograft tissues, the rotation speed ranges from 8 to about 12 revolutions per minute. As will be appreciated by one skilled in the art, a fixed speed or variable speed motor can be utilized for the rotation drive system. In one exemplary embodiment, the rotation drive system comprises a fixed speed motor.

Treatment system 420 in FIG. 6 is also configured to facilitate the exchange of treatment fluids, particularly exchanging treatment fluids without opening the treatment canister. In addition, system 420 is also configured to not only process allografts from two different donors at the same time (using first and second treatment canisters 440A and 440B), but also to perform such processing without risk of cross-contamination between the tissues of different donors. In particular and as shown in FIG. 6, treatment system 420 includes a drainage cradle 432 and a filling cradle 433. A drainage line 434 is provided in fluid communication with drainage cradle 432 such that treatment fluid and waste materials removed from a treatment canister placed into drainage cradle 432 will be drained through drainage hose 434 (for discard or collection and subsequent analysis).

In the embodiment shown in FIG. 6, treatment system 420 is configured to deliver three different treatment fluids to the treatment canisters for allograft processing. Of course, any number of treatment fluids may be used and the treatment system configured accordingly. In the embodiment shown, fluid conduits 461, 463 and 465 are provided in fluid communication with one or more storage tanks for the treatment fluids to be used. These conduits deliver the appropriate treatment fluid to treatment fluid delivery devices 460, 462 and 464, respectively. These delivery devices may simply comprise a secondary storage tank from which the treatment fluid is delivered (e.g., by gravity feed) to manifold 470 for transfer to a treatment canister via fill conduit 471 (e.g., a hose). Alternatively, fluid delivery devices 460, 462 and 464 may each include a fluid pump, a heat exchanger, and/or a filtration system for the corresponding fluid delivered thereto.

Each of the treatment fluid delivery devices is in fluid communication with a manifold 470, which in turn is in communication with treatment fill conduit 471. A waste return conduit 467 is also provided in fluid communication with manifold 470, and may be used to drain excess treatment fluid from manifold 470, as needed. In addition, or as an alternative, waste return conduit 467 may be used to provide sterilize in-place capabilities (e.g., for sterilizing the interior of a treatment canister, manifold 470 or any of the other fluid delivery components depicted in FIG. 6). In the particular embodiment shown in FIG. 6, fluid conduit 461 may be in fluid communication with a source of hydrogen peroxide, conduit 463 in fluid communication with a source of sterilized water, and fluid conduit 465 in fluid communication with a source of isopropyl alcohol.

In one exemplary embodiment, the treatment apparatus is sanitized in place, wherein the apparatus is sanitized using common methods known to these skilled in the art such as flushing the treatment canisters and baskets with heated water (approximately 70° C. for 20 minutes) and/or flushing with chemical sanitization agents.

In order to use treatment system 420 of FIG. 6, allografts to be treated are first placed within one of the treatment canisters 440A or 440B. The ends of the treatment canister (e.g., the treatment canister depicted in FIG. 4) are then sealed and the treatment canister is placed into fill cradle 433. The end of conduit 471 is then connected to an inlet provided on one end of the treatment canister. Treatment fluid is then purged into the treatment canister through conduit 471. Thereafter, the treatment canister is loaded into the carriage, as shown. The other treatment canister may, if desired, be similarly filled with allografts to be treated, as well as the first treatment fluid to be used during allograft treatment. Thereafter, the carriage is lowered into sonication tank 421 and ultrasonic energy applied to the treatment canisters while the treatment canisters are rotated.

After a predetermined amount of time has passed, the carriage is raised out of sonication tank 421 and one of the treatment canisters is removed from the carriage and placed into drainage cradle 432. At least one end of the treatment canister may be configured so as to include a spring-loaded drain. For example, the spring-loaded drain may be configured such that when the treatment canister is inserted into drainage cradle 432 and pressed downwardly, a structure within drainage cradle 432 will act to open the spring-loaded drain. In this manner, used treatment fluid as well as waste materials will be drained from the treatment canister through drainage conduit 434 without the operator opening the treatment canister. Once drained, the treatment canister is then placed into fill cradle 433 and fill conduit 471 is connected thereto. The treatment canister may then be filled with a second treatment fluid (which may be the same or different than the first treatment fluid) or filled with a rinse solution which is thereafter drained from the treatment canister using drainage cradle 432.

It is also contemplated that rinsing or flushing of the interior of the treatment canister may be accomplished while the treatment canister is positioned within drainage cradle 432 (e.g., by delivering a rinse fluid such as sterilized water to the treatment canister via fill conduit 471 while simultaneously or periodically opening the spring-loaded drain provided in the end of the treatment canister). Rinsing and/or flushing of the interior of the treatment canister may be repeated, as desired. Thereafter, the treatment canister is filled with the predetermined treatment fluid according to the predetermined processing steps using fill cradle 433. The treatment canister is returned to the carriage and lowered back into sonication tank 421 for additional treatment. This entire process may be repeated as many times as desired, particularly according to predetermined processing steps.

Figure 7:
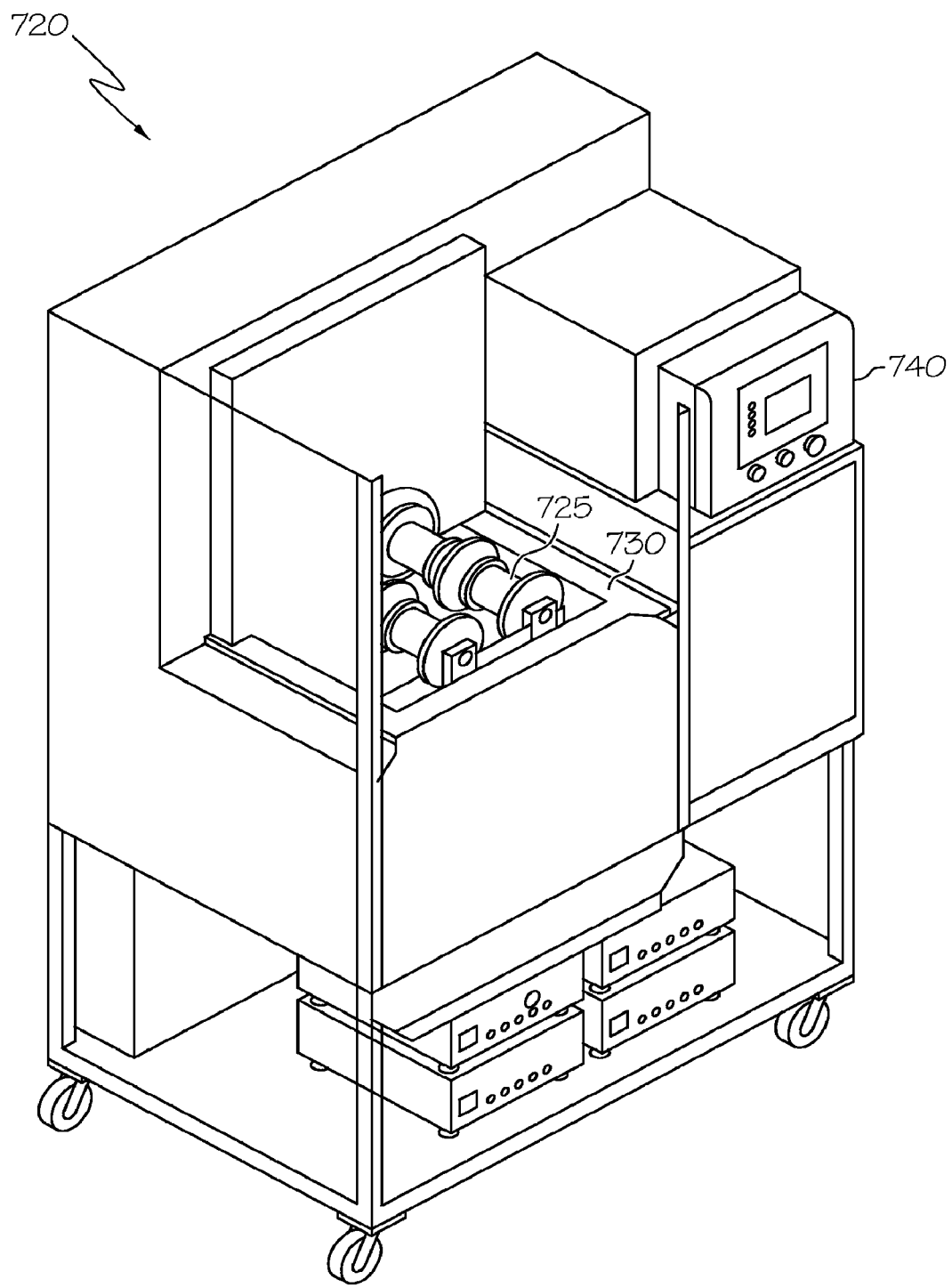
FIG. 7 is a schematic illustration of a treatment system according to one embodiment of the present invention.

Another embodiment of an ultrasonic treatment apparatus 720 is illustrated in FIG. 7 according to the present invention. In this embodiment, the ultrasonic treatment apparatus 720 is configured such that up to four canisters 725 may be simultaneously processed within the sonication tank 730. In this manner, allografts from one to four different donors may be processed simultaneously. In the present embodiment, the apparatus 720 further comprises an operator control interface 740. The operator control interface 740 is configured such that a user can enter desired treatment parameters for the apparatus.

A variety of treatment protocols may be used, regardless of which treatment apparatus is employed. One advantage provided by embodiments of the present invention is that the processing of allografts from beginning to end can be performed in separate rooms or facilities having different sterility standards without jeopardizing allograft sterility.

For example, recovered tissue may first be processed in a recovery room. This processing may include debridement, and the removal of gross musculature, connective tissues and blood elements. The intact tissues are then cut into allograft products. Thereafter, the allografts may be loaded into a treatment canister (e.g., treatment canister 40 from FIG. 1). In some embodiments, the treatment canister may be sealed at this time.

The allograft-loaded treatment canister is then taken to a second facility or room, such as an allograft processing room, for treatment according to the present invention. For example, an allograft-loaded treatment canister may be placed into the sonication tank. Thereafter, the first treatment fluid is automatically pumped into the canister without opening the canister or exposing the allografts thus preserving the integrity of the cleaned allografts as well as minimizing environmental cross-contamination. The allografts are subjected to sonication and rotation according to a predetermined schedule. Periodically, the treatment fluid in the treatment canister may be exchanged, such as by pumping additional treatment fluid (either the same or different from that already in the canister) while allowing the treatment fluid already in the canister to escape (and optionally pumping out the treatment fluid already in the canister).

Following treatment, the allografts, still contained within the sealed treatment canister, may be taken to a third facility or room, such as a packaging room. Here the allografts may be visually inspected, measured and aseptically packaged for subsequent terminal sterilization or delivery to practitioners for use.

EXAMPLES

One process for treating cut allografts (i.e., cortical/cancellous, cancellous, soaking grafts and machine grafts) according to an embodiment of the present invention is as follows:

| Treatment | Time | Temp | Rotation Parameter (rpm) |
|---|---|---|---|
| Step 1: Dry Spin Centrifugation @ 1460 RCF | 3 minutes | N/A | N/A |
| Step 2: Bacitracin/Polymyxin B* | 30 minutes | 45-50° C. | ~10 RPM/104 kHz (100 W/Gal) |
| Step 3: Static Sterile Water Rinse | ~0.5 minutes | 22-40° C. | N/A |
| Step 4: 3% Hydrogen Peroxide | 60 minutes | 45-50° C. | ~10 RPM/104 kHz (100 W/Gal) |
| Step 5: Static Sterile Water Rinse | ~0.5 minutes | 22-40° C. | N/A |
| Step 6: Bacitracin/Polymyxin B | 60 minutes | 45-50° C. | ~10 RPM/104 kHz (100 W/Gal) |
| Step 7: Static Sterile Water Rinse | ~0.5 minutes | 22-40° C. | N/A |
| Step 8: 3% Hydrogen Peroxide | 60 minutes | 45-50° C. | ~10 RPM/104 kHz (100 W/Gal) |
| Step 9: Static Sterile Water Rinse | ~0.5 minutes | 22-40° C. | N/A |
| Step 10: 70% Isopropyl Alcohol | 30 minutes | 45-50° C. | ~10 RPM/104 kHz (100 W/Gal) |
| Step 11: Static Sterile Water Rinse | ~0.5 minutes | 22-40° C. | N/A |
| Total Processing Time | 242.5 min. | | |
| Net Log Reduction | >4 logs | | |

*50 U/mL Bacitracin and 500 U/mL Polymyxin B

One process for treating soft tissue (i.e. ligament and tendon tissues with or without bone blocks) according to an embodiment of the present invention is as follows:

| Treatment | Time | Temp | Rotation Parameter (rpm) |
|---|---|---|---|
| Step 1: Dry Spin Centrifugation @ 1460 RCF | 3 minutes | N/A | N/A |
| Step 2: Polymyxin B (1000 U/mL) | 30 minutes | 45-50° C. | ~10 RPM/104 kHz (100 W/Gal) |
| Step 3: Static Sterile Water Rinse | ~0.5 minutes | 22-40° C. | N/A |
| Step 4: 70% Isopropyl Alcohol | 3 minutes | 45-50° C. | ~10 |
| Step 5: Static Sterile Water Rinse | ~0.5 minutes | 22-40° C. | N/A |
| Step 6: Bacitracin/Polymyxin B* | 30-35 minutes | 45-50° C. | ~10 RPM/104 kHz (100 W/Gal) |
| Step 7: Static Sterile Water Rinse | ~0.5 minutes | 22-40° C. | N/A |
| Total Processing Time | 67.5 min. | | |
| Net Log Reduction | ~3 logs | | |

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

What is claimed is:

1. A method of treating allografts, comprising:
placing one or more allografts inside a treatment canister rotatably mountable in a sonication tank of an ultrasonic treatment apparatus, wherein the sonication tank contains a sonication fluid;
supplying at least one treatment fluid to the interior of the treatment canister while the treatment canister is supported by the sonication tank, wherein the treatment canister is sealed with respect to the sonication tank so as to prevent the at least one treatment fluid from entering the interior of the treatment canister;
transmitting ultrasonic energy to the interior of the tank and the treatment canister with at least one ultrasonic transducer; and
exposing the allografts to the at least one treatment fluid in the treatment canister while exchanging of the at least one treatment fluid with the treatment canister while the treatment canister remains in the sonication tank.

2. A method of treating allografts, comprising:
placing one or more allografts inside a treatment canister rotatably mountable in a sonication tank of an ultrasonic treatment apparatus, wherein the sonication tank contains a sonication fluid;
supplying at least one treatment fluid to the interior of the treatment canister while the treatment canister is supported by the sonication tank, wherein the treatment canister is sealed with respect to the sonication tank so as to prevent the at least one treatment fluid from entering the interior of the treatment canister;
transmitting ultrasonic energy to the interior of the tank and the treatment canister with at least one ultrasonic transducer;
exposing the allografts to the at least one treatment fluid in the treatment canister while simultaneously rotating the treatment canister and exchanging the at least one treatment fluid with the treatment canister while the treatment canister remains in the sonication tank.

3. A method of treating allografts, comprising:
placing one or more allografts inside a treatment canister rotatably mountable in a sonication tank of an ultrasonic treatment apparatus, wherein the sonication tank contains a sonication fluid;
supplying at least one treatment fluid to the interior of the treatment canister while the treatment canister is supported by the sonication tank, wherein the treatment canister is sealed with respect to the sonication tank so as to prevent the at least one treatment fluid from entering the interior of the treatment canister;
transmitting ultrasonic energy to the interior of the tank and the treatment canister with at least one ultrasonic transducer; and
exposing the allografts to the at least one treatment fluid in the treatment canister while exchanging of the at least one treatment fluid with the treatment canister while the treatment canister remains rotatably mounted in the sonication tank of an ultrasonic treatment apparatus.

4. A method of treating allografts, comprising:
placing one or more allografts inside a treatment canister rotatably mountable in a sonication tank of an ultrasonic treatment apparatus, wherein the sonication tank contains a sonication fluid;
supplying at least one treatment fluid to the interior of the treatment canister while the treatment canister is supported by the sonication tank, wherein the treatment canister is sealed with respect to the sonication tank so as to prevent the at least one treatment fluid from entering the interior of the treatment canister;
transmitting ultrasonic energy to the interior of the tank and the treatment canister with at least one ultrasonic transducer; and
exposing the allografts to the at least one treatment fluid in the treatment canister while simultaneously rotating the treatment canister and exchanging the at least one treatment fluid with the treatment canister while the treatment canister remains rotatably mounted in the sonication tank of an ultrasonic treatment apparatus.

5. A method of treating allografts, comprising:
placing one or more allografts inside a treatment canister rotatably mountable in a sonication tank of an ultrasonic treatment apparatus, wherein the sonication tank contains a sonication fluid;
supplying at least one treatment fluid to the interior of the treatment canister while the treatment canister is supported by the sonication tank, wherein the treatment canister is sealed with respect to the sonication tank so as to prevent the at least one treatment fluid from entering the interior of the treatment canister; and
transmitting ultrasonic energy to the interior of the tank and the treatment canister with at least one ultrasonic transducer;
wherein the treatment canister is sealed with respect to the sonication tank, and a sonication fluid is provided in the tank.

6. A method of treating allografts, comprising:
placing one or more allografts inside a treatment canister rotatably mountable in a sonication tank of an ultrasonic treatment apparatus, wherein the sonication tank contains a sonication fluid;
supplying at least one treatment fluid to the interior of the treatment canister while the treatment canister is supported by the sonication tank, wherein the treatment canister is sealed with respect to the sonication tank so as to prevent the at least one treatment fluid from entering the interior of the treatment canister; and
transmitting ultrasonic energy to the interior of the tank and the treatment canister with at least one ultrasonic transducer;
providing a treatment fluid within the treatment canister; and
exchanging at least a portion of the treatment fluid in the treatment canister without removing the allografts from the treatment canister.

7. A method of treating allografts, comprising:
placing one or more allografts inside a treatment canister rotatably mountable in a sonication tank of an ultrasonic treatment apparatus, wherein the sonication tank contains a sonication fluid;
supplying at least one treatment fluid to the interior of the treatment canister while the treatment canister is supported by the sonication tank, wherein the treatment canister is sealed with respect to the sonication tank so as to prevent the at least one treatment fluid from entering the interior of the treatment canister; and
transmitting ultrasonic energy to the interior of the tank and the treatment canister with at least one ultrasonic transducer;
wherein the ultrasonic treatment apparatus further includes a fluid control system adapted for exchanging the first treatment fluid for the second treatment fluid.

8. A method of treating allografts, comprising:
placing one or more allografts inside a treatment canister rotatably mountable in a sonication tank of an ultrasonic treatment apparatus, wherein the sonication tank contains a sonication fluid;
supplying at least one treatment fluid to the interior of the treatment canister while the treatment canister is supported by the sonication tank, wherein the treatment canister is sealed with respect to the sonication tank so as to prevent the at least one treatment fluid from entering the interior of the treatment canister; and
transmitting ultrasonic energy to the interior of the tank and the treatment canister with at least one ultrasonic transducer;
further comprising the step of removing the treatment fluid from the treatment canister and filtering at least a portion of the removed treatment fluid.

* * * * *